United States Patent [19]

Bales

[11] Patent Number: 4,459,482

[45] Date of Patent: Jul. 10, 1984

[54] AUGER SPECTROSCOPIC TECHNIQUE MEASURING THE NUMBER OF ELECTRONS EMITTED FROM A SURFACE AS A FUNCTION OF THE ENERGY LEVEL OF THOSE ELECTRONS

[76] Inventor: Maurice J. Bales, 10 Middle Rd., Lafayette, Calif. 94549

[21] Appl. No.: 375,496

[22] Filed: May 6, 1982

[51] Int. Cl.³ .......................... H01J 40/00; H01J 47/00
[52] U.S. Cl. .................................................. 250/305
[58] Field of Search ................. 250/305, 310; 307/359

[56] References Cited

U.S. PATENT DOCUMENTS 3,461,306  8/1969  Stout et al.
3,914,606  10/1975  Hashimoto et al. ............... 250/305
4,145,743  3/1979  Di Ciurcio ......................... 307/359

FOREIGN PATENT DOCUMENTS 53-123996  3/1978  Japan ................................. 250/305
197511  11/1975  U.S.S.R. ............................ 250/305

OTHER PUBLICATIONS

"Toward Optimum Utilization of the Cylindrical Mirror Analyzer in Auger Electron Spectroscopy", Pocker, *Rev. Sci Ins.*, vol. 46, No. 1, Jan. 1975, pp. 10–106.

"Digital Data Acquisition and Processing in an Auger Electron Spectrometer", Strausser, *Applied Surface Anal.*, 1980, pp. 158–181.

"Linearized secondary-electron cascades from the surfaces of metals, I, Clean surfaces of homogeneous specimens", Sickafus, *Physical Review B*, vol. 16, No. 4, 8–77, pp. 1436–1447.

*Primary Examiner*—Bruce C. Anderson
*Attorney, Agent, or Firm*—Majestic, Gallagher, Parsons & Siebert

[57] ABSTRACT

An improved technique in Auger electron spectroscopy which uses a standard detector which emits a voltage signal proportional to the number of electrons emitted from a surface of material under investigation at a particular energy level to which the detector is set. An improvement is in the manner of processing this voltage signal in order to ascertain the desired reading of number of electrons. The processing circuitry is electrically isolated from the rest of the system but is directly coupled to the detector. A baseline voltage signal is established at a lower edge of electron energy range of interest and that range has been scanned to determine the difference between detector signal output and the baseline output. The result is a faster and more accurate determination of detector voltage signal outputs over the region which can then better be used to determine the characteristics of the surface from which the electrons are being emitted.

6 Claims, 3 Drawing Figures

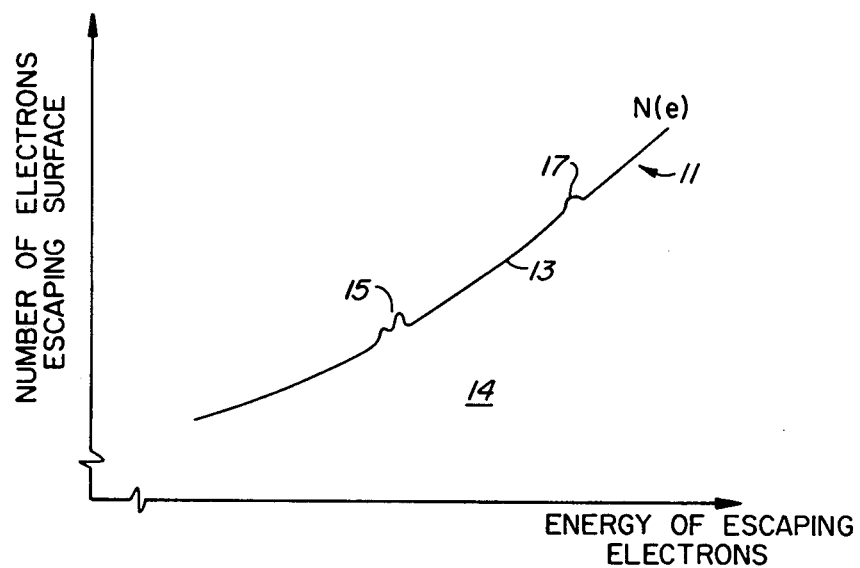
FIG._1.
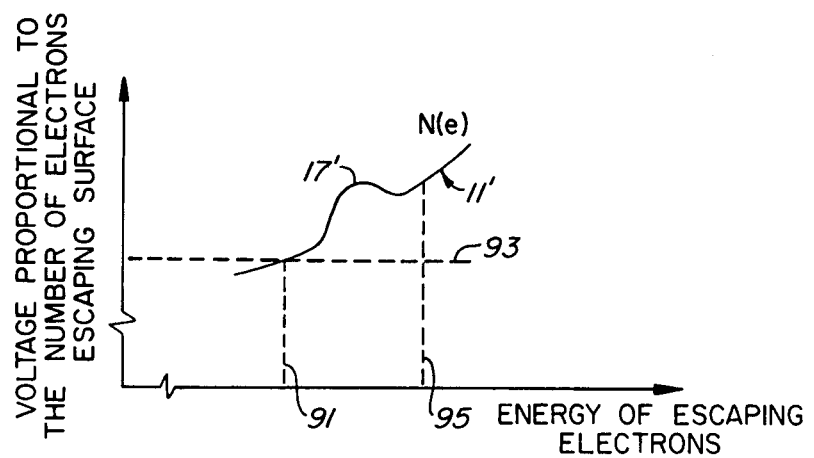
FIG._3.

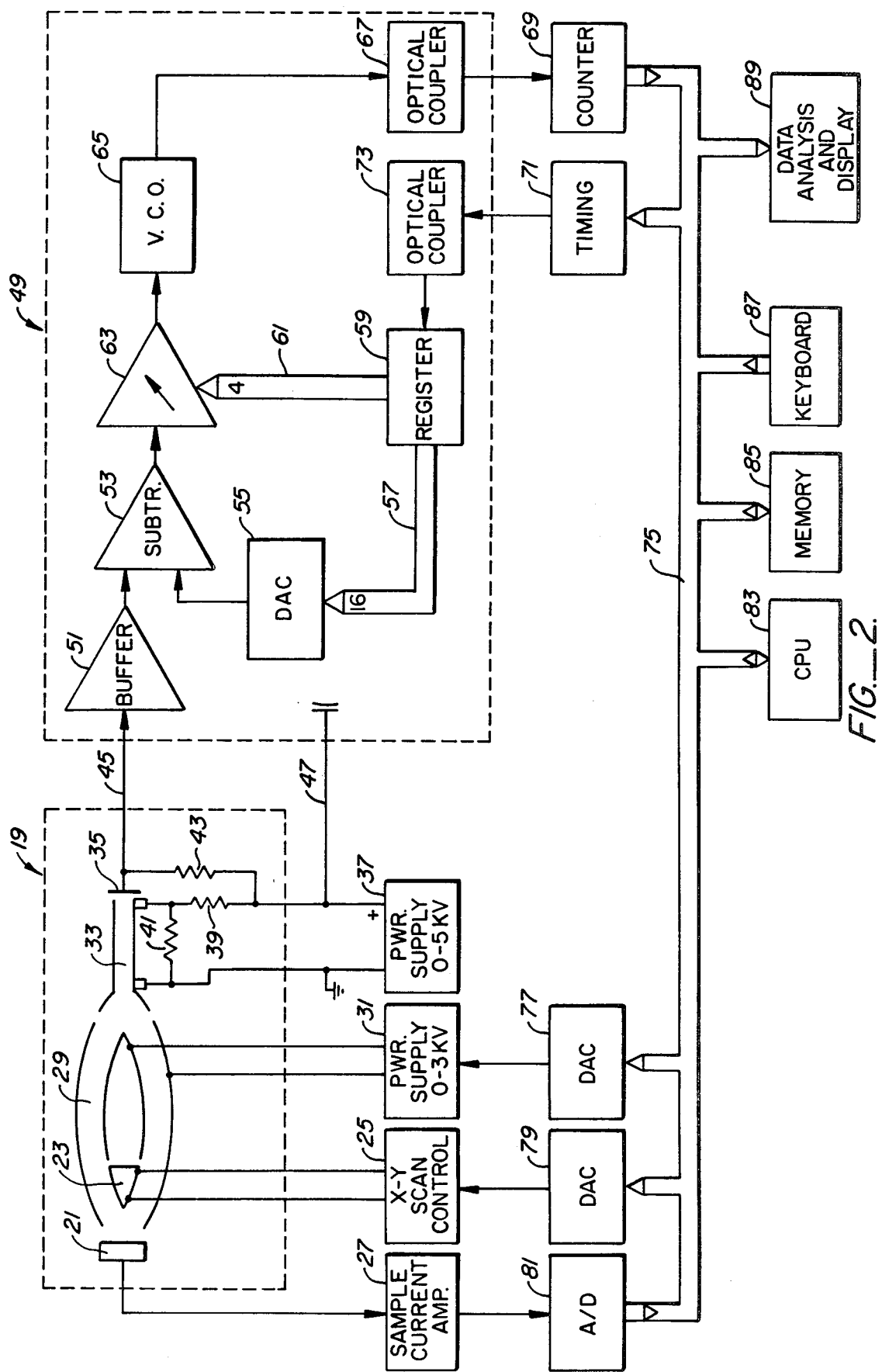
FIG._2.

AUGER SPECTROSCOPIC TECHNIQUE MEASURING THE NUMBER OF ELECTRONS EMITTED FROM A SURFACE AS A FUNCTION OF THE ENERGY LEVEL OF THOSE ELECTRONS

BACKGROUND OF THE INVENTION

This invention relates generally to Auger spectrometry, and more particularly to an electronic system for measuring the number of electrons emitted from a surface under investigation from a signal output of an electron detector.

Auger spectroscopy is a technique for determining the composition of a material surface by bombarding that surface with an electron beam and then detecting the electrons emitted from it. A spectra of a quantity of electrons emitted as a function of their energy can tell the characteristics of the material. These Auger electron lie in an energy level that extends gernerally between the low energy level of the emission of secondary electrons up to the energy of the impinging electron beam. In this region, small peaks will occur in the spectra at certain energy levels that identifies the existence of certain elements in the surface. A particular application of Auger spectroscopy is to examine the depths of a material upon peeling layers away and examining the new surface.

Available detectors, such as a cylindrical analyzer, coupled with an electron multiplier, provides a voltage signal at its collector that is proportional to the number of electrons that have entered the detector with an energy level equal to the voltage to which the detector is set. Because high voltages are necessary to operate the detector and multiplier, the voltage variation at the output of the detector that is desired to be measured, within a small fraction of one volt, are superimposed on hundreds or even thousands of volts. The problem in measuring a spectra under these circumstances is that the small voltage variations, which give an indication of the materials present, are lost in system noise, drift, etc.

One approach that has been taken in the past to extract the desired small peaks from the total amount of output signal is to measure the voltage drop across a load resistor at an output of the electron multiplier. Since this signal is superimposed on the several hundred or thousands of volts of the electron multiplier power supply, an isolation amplifier, chopper and analog optical coupler are used so that the desired voltage signal can be processed with respect to ground potential according to normal techniques. But the accuracy of these techniques is still not satisfactory because of drift and linearity inaccuracies of these coupling components. The measurement also takes a considerable time to accomplish by digital counting techniques.

Another approach that is utilized to overcome the problem is to differentiate the signal output of the electron multiplier in order to detect the location of the small voltage peaks in the baseline voltage curve. But this technique also suffers from an inability to detect very small signals and further does not enable the observer to determine the area of the peaks above the baseline, a desired quantity for certain analytical work.

Yet another technique for determining where the peaks of interest lie is to substract from the spectra signal a signal representing the baseline. However, this also has difficulties in detecting the peaks because of the high level of noise with respect to the level of the signal to be detected.

Therefore, it is a primary object of the present invention to provide a technique of processing an output signal of an Auger spectrometer detector which is fast, accurate and simple.

SUMMARY OF THE INVENTION

This and additional objects are accomplished by the various aspects of the present invention wherein, briefly, the electron detector output signal is directly coupled to processing electronics by using the high voltage power supply positive terminal as a common potential for this processing circuitry. No isolation amplifier, optical coupler, or the like, is utilized, thereby eliminating errors that can be introduced by such elements through drift and non-linearity. Such coupling occurs at the output of the signal processor where the signal-to-noise ratio is now much higher, and may be in digital form to further immunize the signal from noise.

To further reduce inaccuracy, the detection of voltage signals having a magnitude in the order of tens of microvolts within the several volts detector output signal is made possible by looking at a small part of the spectra at a time and by defining a baseline just below a desired spectra portion. That portion is then scanned and a difference between the detector output voltage and this reference baseline voltage is determined. Since use of a digital counter is a preferred way of measuring this voltage difference, a number of measurements can be made at different electron energy levels in a short amount of time, as well as with increased accuracy. This procedure is repeated for other segments of the spectra that are of interest for examination.

Additional objects, advantages and features of the present invention will become apparent from the following description of its preferred embodiments, which description should be taken in conjunction with the accompanying drawings.

BRIEF DESCRIPTION OF THE DRAWINGS

FIG. 1 is a curve that is an example of an electron spectra in the Auger electron region;

FIG. 2 is a block diagram schematic of an electron system embodying the various techniques of the present invention; and FIG. 3 is a curve that illustrates the operation of a portion on the circuit of FIG. 2.

DESCRIPTION OF A PREFERRED EMBODIMENT

Referring initially to FIG. 1, a typical electron spectra curve 11 is shown for the purposes of explanation. On the vertical axis is represented the number of electrons entering a detector of a type to be described with respect to FIG. 2. On the horizontal axis is the energy level of the electrons so detected. A baseline portion 13 generally follows the shape of a fourth power curve. Small peaks 15 and 17 are shown as representing Auger electrons at different energy levels. The specific energy levels of these peaks give information as to the composition of the surface from which the electrons are emitted. The shape and area of these peaks is also often of interest in analyzing material surfaces.

Referring to FIG. 2, a standard type of Auger spectrometer detector 19 is illustrated. The elements within the dotted outline are contained within an ultra high vacuum. A sample material 21 is bombarded with a stream of electrons from an electron gun 23 that is scanned across a surface of the sample 21 in response to signals from control circuits 25. Amplifier 27 receives current from the specimen 21. The surface of the sample 21 emits electrons, in response to being bombarded by a stream of electrons from the gun 23, which enter a cylindrical mirror analyzer 29 which detects all electrons emitted from a surface that have an energy level equal to the voltage of a detector power supply 31. An electron multiplier 33 then multiplies the number of electrons so captured by the detector, so that a measurable number strike a collector 35. A power supply 37 is connected through bias resistors 39 and 41 to the electron multiplier 33. Load resistor 43 is connected to a conductor 45 that is, in turn, connected to the collector 35 and thus is of the same potential as the collector (0 –5 kv.).

It is the information of the curve 11 of FIG. 1 that is carried in the voltage signal 45 as the power supply 31 is swept across the Auger electron emitting portion of the spectrum. However, as discussed previously, the desired peaks 15 and 17 are usually a small fraction of a volt, while the potential at conductor 45 (FIG. 2) is usually thousands of volts with respect to ground potential. Thus, such small signal peaks 15 and 17 are lost in the noise of the system. One technique that has been recognized in the past is to measure the output signal in the conductor 45, not with respect to ground potential, but with respect to the potential of the positive terminal in the power supply 37, to which a conductor 47 has been attached. The desired signal peaks 15 and 17 (FIG. 1) are then floating on only a few volts and thus can be easier to detect than if measured with respect to ground where they float on several thousand volts. But these prior techniques have utilized isolation amplifiers, optical couplers, and the like in order to convert these voltage variations to a ground potential reference signal. Noise introduced by these elements and their nonlinearities have rendered it very difficult to detect these small voltage peaks 15 and 17. This is particularly true where the voltage resolution of the instrument is to be tens of microvolts, as in practical applications of the various aspects of the present invention.

The Auger electrons are the small perturbations 15 and 17 of the curve 11 (FIG. 1). The area 14 below the curve 11 is secondary electrons which are not representative of the characteristics of the material.

Referring to FIG. 2, an electronic circuit 49 receives the voltage signal between lines 45 and 47 and processes it in order to discover whether any small voltage peaks exist, such as the peaks 15 and 17 (FIG. 1). The elements of the circuit 49 within the dotted outline of FIG. 2 all use as a reference potential that of the positive terminal of the power supply 37 by being connected to the line 47. All electronic circuits have a common potential to which the various circuit elements are connected, this usually being ground potential. But here, the circuit 49 remains floating from the rest of the instrument and has the several thousand volt reference. A power supply (not shown) for the elements of the circuit 49 is also isolated from ground potential.

A buffer amplifier 51 is provided as an input element to the circuit 49 in order to avoid loading the output of the detector 19. An output of the buffer 51 forms one of two inputs to a substraction circuit 53. Another input of the subtractor 53 is an output of a digital-to-analog converter 55 which is set by a digital signal in circuits 57 from a register 59. The register 59 also provides a control signal in digital circuits 61 that sets the gain of an amplifier 63 so that the difference between the signal outputs of the DAC 55 and buffer amplifier 51 is within an operating range of a voltage controlled oscillator 65. A pulse train from the oscillator 65 is passed through an optical coupler 67 to a digital counter 69 that is external of the circuit 49. Similarly, control input signals are provided from timing logic circuits 71 through an optical coupler 73, provided as part of the isolated circuit 49, whose output is applied to the register 59. The register 59 is a serial-to-parallel converter.

Before explaining the operation of the circuit 49 in detail, the remainder of the system of FIG. 2 will be briefly outlined. A common system bus 75 receives the state of the counter 69 and applies control signals to the timing circuits 71 for transmittal to the register 59. Similarly, a digital-to-analog converter 77 is connected to the bus for receiving commands to set the power supply 31 to the desired level of energy at which emitted electrons from the surface of the sample 21 are to be detected at any given instant. Another digital-to-analog converter 79 receives commands from the common bus 75 for directing the control circuit 25 to properly position the electron gun 23 for scanning across the surface for the sample 21 under investigation. An analog-to-converter 81 receives the output of the sample current amplifier 27 and gives a digital representation of it for use by controlling elements of the system.

As is typical in such an architecture, the common bus 75 has a controlling central processing unit 83 connected to it, its central element being a microprocessor. Adequate memory 85 of an appropriate type or types is also connected to the system bus. Information and commands are entered into the system through a keyboard 87, connected to the system bus 75, and information on that bus as to the results of a test is displayed or recorded in a desired manner by a device 89. The analysis and display circuits 89 can be anything from a simple digital readout to a more complicated two dimensional picture of the sample surface, either on a cathode ray tube or through a graphic plotter, in a manner showing the various Auger electrons emitted across the sample surface in two dimensions.

Referring to the curve of FIG. 3, the operation of the isolation circuit 49 will now be explained. The curve 11' represents the voltage at the conductor 45 with respect to the reference conductor 47. A small voltage peak 17' is desired to be detected. It is generally known, for a given sample surface, where a peak is likely to occur. A voltage level 91 of the power supply 31 is selected by the operator of the instrument to be slightly below the region of interest in which a peak is suspected. This will give a baseline voltage 93 at the conductor 45, with respect to the reference potential on the conductor 47. It is this voltage that is presented to the substracting circuit 53 at the output of the DAC 55 as set by the register 59 and timing circuit 71. The voltage of the analyzer 29 is then stepped from electron-volt (ev) 91, through control of the power supply 31, in small increments for an interval to ev 95, for example. During this stepping process, the varying voltage in the line 45 causes the frequency of pulses emitted by the oscillator 65, and thus driving the counter 69, to vary as a function of the voltage waveform 11'. During this sweep, the voltage output of the DAC 55, being the voltage level 93, remains constant. After this region is scanned, the operator can reset the instrument to scan the same or new energy which corresponds to a particular chemical element.

What the technique illustrated in FIG. 3 accomplishes is the extraction of very small Auger peaks on the several volts of the signal 11' which is a secondary electron background base. The small voltage peak 17' is, as a percentage of such base voltage, increased considerably by use of the new baseline 93 to which it is measured. The small voltage peak 17' is more easily and accurately detected in this manner. Controlling software for accomplishing the setting of the reference voltage 93 and scanning between electron energy voltages of 91 and 95, is given by an Appendix hereto.

Although the various aspects of the present invention have been described with respect to a preferred embodiment thereof, it will be understood that the invention is entitled to protection within the full scope of the appended claims.

It is claimed:

1. In a method of Auger spectroscopy wherein a material surface whose characteristics are desired to be determined is bombarded by an electron beam and a resulting quantity of Auger electrons emitted from the surface are measured as a function of their energy level, the improvement comprising the steps of:
   (a) Determining a small region of interest of energy level for emitting electrons;
   (b) Determining a base line number of electrons emitted from the material that is at or near a lower edge of said energy region of interest; and
   (c) Determining the difference between the actual number of electrons emitted from the material at various energy levels within said region of interest and the baseline number of electrons,
whereby these differences are accurately and quickly determined over the region of interest in order to detect the existence and shape of any small peaks in the number of electrons emitted within said small region.

2. The improved method according to claim 1 wherein steps (a), (b) and (c) are repeated for a second region of interest of electron energy that is non-overlapping with the first region.

3. The improved method according to claim 1 wherein each of the steps (b) and (c) are accomplished by detecting voltage level of a magnitude proportional to the number of electrons being detected to be emitted from said surface, said voltage level being referenced to a high voltage supply of an electron detecting system.

4. In an Auger spectroscopic system of a type having a detector of electrons at various selectable energy levels coupled with an electron multiplier that is operated with a high voltage supply, a voltage level of an electron collector at the output of the electron multiplier giving an indication of the number of electrons entering the detector at the selected energy level, an improved electronic system for detecting and measuring the number of electrons through said collector voltage level, comprising:
   means directly coupled to the electron collector for receiving a voltage signal between the collector and a positive terminal of the high voltage supply, said voltage signal being proportional to the number of Auger electrons being detected,
   means responsive to a designation of an operator for establishing a baseline reference voltage at one of many particular selectable levels representing a number of background electrons normally detected at the selected energy level, and
   means receiving said voltage signal and said baseline reference voltage for determining a difference voltage there between over at least a portion of the range of electron energy level selectable by said detector,
whereby the existence of peaks in energy level can be identified with a high degree of accuracy.

5. The improved detecting and measuring system according to claim 4 wherein claim said baseline reference voltage establishing means and said difference determining means are isolated from ground potential, each having a common connected to a positive terminal of said electron multiplier high voltage supply, and additional measuring and central circuits operating with reference to ground potential being connected therewith through electrical isolating elements.

6. For an Auger electron detector capable of measuring electrons emitted from a sample surface at various selectable energy levels, an improved electronic system for processing a signal output of the detector in order to determine the number of electrons entering said detector at various energy levels, comprising:
   means responsive to a designation for establishing a baseline reference signal corresponding to a particular number of background electrons normally detected at a particular energy level, and
   means receiving detector signal and said baseline signal for determining a difference there between over at least a portion of a range of electron energy level selectable by said detector, whereby peaks and energy levels can be measured quickly with a high degree of accuracy.

* * * * *